(12) United States Patent
Mattes et al.

(10) Patent No.: US 10,575,942 B2
(45) Date of Patent: Mar. 3, 2020

(54) FLEXIBLE, HERMETIC ELECTRICAL INTERCONNECT FOR ELECTRONIC AND OPTOELECTRONIC DEVICES FOR IN VIVO USE

(71) Applicant: Novartis AG, Basel (CH)

(72) Inventors: Michael F. Mattes, Chandler, AZ (US); Mark A. Zielke, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/112,853

(22) Filed: Aug. 27, 2018

(65) Prior Publication Data

US 2018/0360595 A1 Dec. 20, 2018

Related U.S. Application Data

(62) Division of application No. 14/968,050, filed on Dec. 14, 2015, now Pat. No. 10,092,396.

(51) Int. Cl.

| | |
|---|---|
| *A61F 2/16* | (2006.01) |
| *A61N 1/375* | (2006.01) |
| *A61N 1/36* | (2006.01) |
| *B29D 11/00* | (2006.01) |
| *G02C 7/08* | (2006.01) |
| *B29D 11/02* | (2006.01) |
| *H05K 3/00* | (2006.01) |
| *H05K 3/28* | (2006.01) |
| *H05K 3/40* | (2006.01) |

(52) U.S. Cl.
CPC ........ *A61F 2/1624* (2013.01); *A61N 1/36046* (2013.01); *A61N 1/3754* (2013.01); *B29D 11/00807* (2013.01); *B29D 11/00817* (2013.01); *B29D 11/00826* (2013.01); *B29D 11/023* (2013.01); *G02C 7/083* (2013.01); *H05K 3/007* (2013.01); *H05K 3/28* (2013.01); *H05K 3/4038* (2013.01); *A61F 2/16* (2013.01); *A61F 2002/1681* (2013.01); *A61F 2220/0025* (2013.01); *A61F 2250/0069* (2013.01)

(58) Field of Classification Search
None
See application file for complete search history.

(56) References Cited

U.S. PATENT DOCUMENTS

| | | | |
|---|---|---|---|
| 2009/0033863 A1* | 2/2009 | Blum | A61F 2/14 351/159.34 |
| 2012/0112347 A1* | 5/2012 | Eckhardt | H01L 21/6835 257/751 |
| 2015/0036302 A1* | 2/2015 | Tai | H01L 23/3135 361/752 |

* cited by examiner

*Primary Examiner* — Shaun M Campbell (57) ABSTRACT

An electronic device can comprise a first electronic module; a second electronic module; and a hermetic electric interconnect to hermetically couple them. The hermetic electric interconnect can comprise a bottom metal layer; a bottom insulating layer, deposited on the bottom metal layer to insulate the bottom metal layer; an interconnect metal layer, deposited on the bottom insulating layer, and deposited to form a bottom sealing ring; and patterned to form electrical connections between contact pads, and to form a middle sealing ring; a patterned top insulating layer, deposited on the interconnect metal layer to insulate the interconnect metal layer; and patterned to form feedthrough holes; and a top metal layer, deposited on the top insulating layer to start forming contacts by filling the feedthrough holes; and patterned to complete forming contacts through the feedthrough holes, to form a separate barrier layer, and to complete forming the top sealing ring.

14 Claims, 11 Drawing Sheets

FLEXIBLE, HERMETIC ELECTRICAL INTERCONNECT FOR ELECTRONIC AND OPTOELECTRONIC DEVICES FOR IN VIVO USE

TECHNICAL FIELD

This patent document is related to electronic and optoelectronic devices. In more detail, this patent document related to (opto-) electronic devices that include a hermetic flexible interconnection for in vivo use.

BACKGROUND

To our knowledge, up to date in-vivo electrical connections were only developed for pacemaker applications. The pacing lead is connected to the pacing device with a receptacle-and-plug type connection. Reliability is often insured by using a set-screw to keep the plug in place, as described, for example, in U.S. Pat. No. 4,764,132. In these devices, non-corrosive metals, insulation, and moisture barriers are used to maintain a projected lifetime of up to 10 years. These connections are large and not hermetic. Therefore, unfavorable leakage currents can be induced during the operation of the device. These leakage currents are often mitigated through the use of insulation and distance. Leakage currents are also not as critical in pacemaker applications since the leads only carry current when the device is sending a pacing pulse.

Recently, various electro-active intraocular lens (EA-IOL) systems have been proposed. These EA-IOLs will also need electronic connections for in vivo use. However, in an EA-IOL there is no room for the large electrical connections of the pacemakers. In addition, the power supplies of these EA-IOLs are typically quite small, they are continuously operated, and all electronic modules are quite close to each other. To avoid leakage currents, and moisture ingress, followed by corrosion, in such systems, the electronic connections and the conductors between connections must be completely isolated from the in vivo environment via a hermetic interconnection scheme.

Somewhat related interconnect schemes have been proposed in the past, such as a high-density, chip-level integrated interconnect packaging system in the article "Microelectronic Packaging for Retinal Prostheses" by D. C. Rodger and Y-C. Tai, in IEEE Engineering in Medicine and Biology Magazine, p. 52, September 2005. However, the described scheme applies a polymer layer (parylene) as the hermetic coating and thus suffers from moisture ingress over time causing leakage currents and eventually, corrosion of the interconnects and connecting wires.

For at least the above reasons, hermetically sealed interconnects are needed that are small enough for implantation into an eye, essentially eliminate leakage currents even when the electronic modules are situated close to each other, and provide reliable sealing for about 10 years even when exposed to the salinity conditions of biological tissue.

SUMMARY

Embodiments in this patent document address the above challenges by introducing a structure and method to fabricate a corrosion proof, or hermetic, flexible interconnect between electronic modules to be implanted for in-vivo use. In some embodiments an electronic device can comprise a first electronic module; a second electronic module; and a hermetic electric interconnect to provide a hermetically sealed electric coupling between the first and second electronic module.

In some embodiments, the hermetic electric interconnect can comprise a bottom metal layer; a bottom insulating layer, deposited on the bottom metal layer to insulate the bottom metal layer, and patterned to form a bottom seal ring trench; an interconnect metal layer, deposited on the bottom insulating layer, and deposited to fill the bottom seal ring trench to form a bottom sealing ring; and patterned to form electrical connections between contact pads, and to form a middle sealing ring around the electrical connections, coupled with the bottom sealing ring; a patterned top insulating layer, deposited on the interconnect metal layer to insulate the interconnect metal layer, and to separate the middle sealing ring from the interconnect metal layer; and patterned to form feedthrough holes for the contact pads, and to form a top seal ring trench coupled with the middle sealing ring; and a top metal layer, deposited on the top insulating layer to start forming contacts by filling the feedthrough holes, and deposited to start forming a top sealing ring by filling the top seal ring trench; and patterned to complete forming contacts through the feedthrough holes, to form a separate barrier layer, and to complete forming the top sealing ring.

In some embodiments, a method of fabricating a hermetic electric interconnect for an optoelectronic device can comprise the steps of: depositing a bottom metal layer on a wafer or substrate; depositing a bottom insulating layer on the bottom metal layer to insulate the bottom metal layer; and patterning the bottom insulating layer to form a bottom seal ring trench; depositing an interconnect metal layer on the bottom insulating layer, to fill the bottom seal ring trench to form a bottom sealing ring; and patterning the interconnect metal layer to form electrical connections between contact pads, and to form a middle sealing ring around the electrical connections; depositing a top insulating layer on the interconnect metal layer to insulate the interconnect metal layer, and to separate the middle sealing ring from the interconnect metal layer; and patterning the top insulating layer to form feedthrough holes coupled with the contact pads, and to form a top sealing ring trench coupled with the middle sealing ring; depositing a top metal layer on the top insulating layer to start forming contacts by filling the feedthrough holes, and to start forming a top sealing ring by filling the top seal ring trench; and patterning the top metal layer to complete forming contacts through the feedthrough holes, to form a separate barrier layer, and to complete forming the top sealing ring, coupled with the middle sealing ring; and seating contact pads of a first electronic module and a second electronic module into the contacts, and seating a module sealing ring into the top sealing ring.

In some embodiments, a method of fabricating a hermetic electric interconnect for an optoelectronic device can comprise the steps of: forming a planarized structure from a first electronic module and a second electronic module with exposed electronic contact pads; depositing a module metal layer on the planarized structure, and patterning the deposited module metal layer to have feedthrough holes, coupled with the electronic contact pads of the first and second electronic modules; depositing a first insulating layer on the module metal layer to insulate the module metal layer, and patterning the deposited first insulating layer to insulate an inner surface of the feedthrough holes; depositing an interconnect metal layer on the first insulating layer and into the feedthrough holes to form contacts, and patterning the deposited interconnect metal layer to form electrical connects between the contacts corresponding to the contact pads of the first and the second electronic modules; depositing a second insulating layer on the interconnect metal layer to seal the interconnect metal layer; and depositing a final barrier layer on the second insulating layer to complete the hermetic seal of the electric interconnect.

DETAILED DESCRIPTION

Embodiments described herein address the above needs and challenges by introducing an electronic or optoelectronic device that has a hermetic electric interconnect to provide hermetically sealed electric connections between electronic modules of the (opto-) electronic device. Embodiments of this (opto-) electronic device have various advantageous aspects, including the followings.

(1) Embodiments can provide long-lifetime biocompatible environmental protection to the electronic modules and their electric connections. Embodiments can be corrosion-proof over 10 years, or 20 years, thus enabling the implantation of this device for long term in-vivo use.

(2) Embodiments can be fabricated using semiconductor batch fabrication technologies which results in low manufacturing costs.

(3) The thin film deposition techniques adapted from semiconductor manufacturing technology are very mature in terms of process quality and control.

(4) A wide range of materials can be utilized using these thin film deposition technologies, such as metals and ceramics.

(5) Embodiments can be miniaturized to extremely small dimensions.

(6) In some embodiments the hermetic interconnect can be flexible. The flexibility can minimize the size of the ophthalmic incisions necessary for insertion. Furthermore, embodiments can adapt to body motion, tissue softness, and the potential evolution of the shape of the surrounding tissues.

(7) Embodiments can have a modular design of the device that allows adding peripherals to the device after the original implantation. Such peripherals can include distant modules, sensing modules (such as chemical, mechanical and electrical sensors), and functionally active modules (such as accommodating lenses and electrodes for nerve stimulation).

(8) Embodiments prevent unintended negative effects such as current leakage between connections and voltage breakdown of dielectric materials due to moisture ingress.

Figure 1:
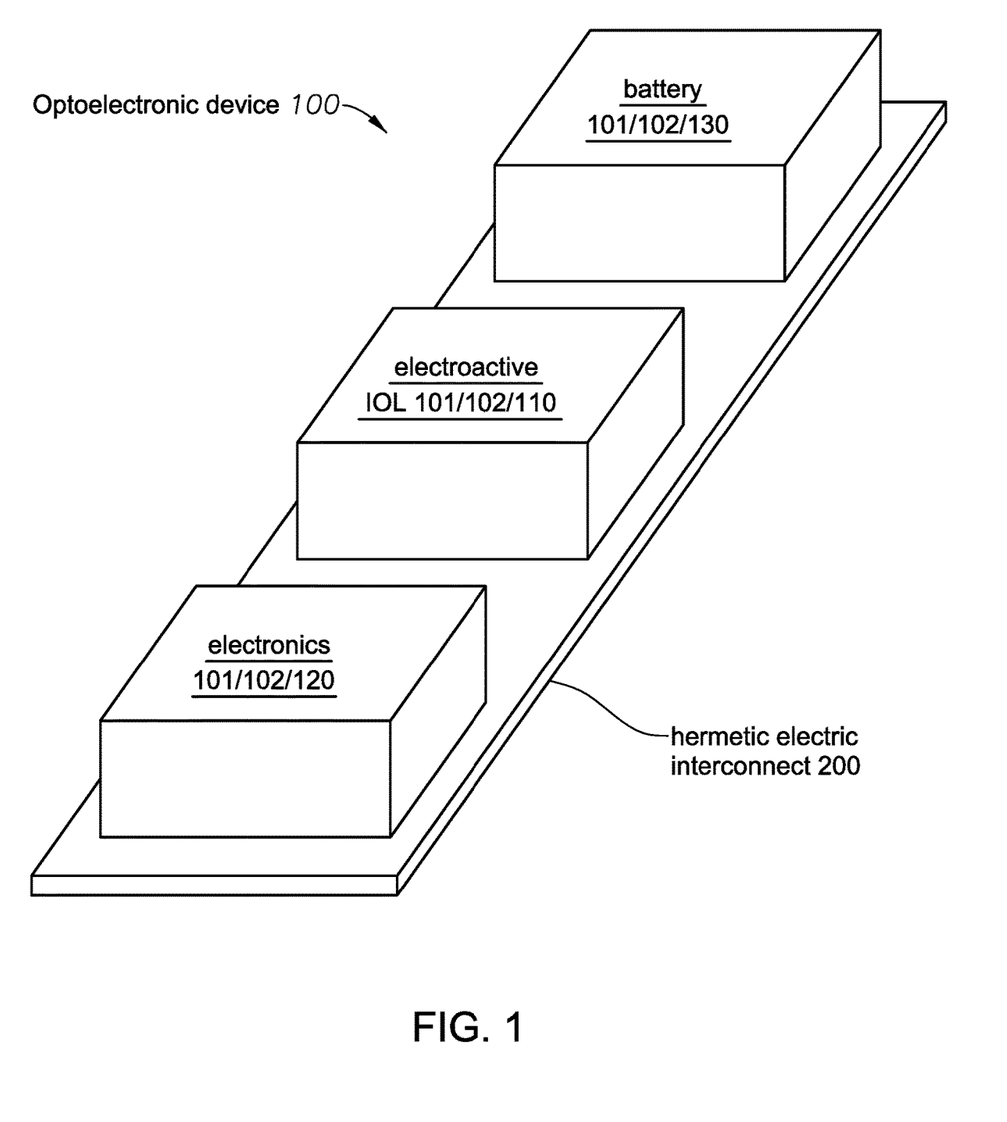
FIG. 1 illustrates an optoelectronic device 100 with a hermetically sealed electric interconnect 200.

FIG. 1 illustrates an embodiment of an optoelectronic device 100 that includes a first electronic module 101, a second electronic module 102, and a hermetic electric interconnect 200 to provide a hermetically sealed electric coupling between the first and second electronic modules 101 and 102. In an Electro-Active Intra-Ocular Lens implementation (EA-IOL) the first electronic module 101 and the second electronic module 102 can be any one of an EA-IOL 110, an electronics module 120, or a battery pack 130. To represent that the first and second electronic modules can be any of these elements, the IOL was labeled 101/102/110, the electronics 101/102/120, and the battery 101/102/130. In other embodiments, the first or the second electronic modules 101 and 102 can be a hermetically sealed enclosure of a combination of integrated circuits and devices. This specification is formulated in terms of optoelectronic devices. However, analogous embodiments can be implemented in non-ophthalmic electronic devices for in vivo use as well.

In some embodiments, the hermetic electric interconnect 200 can be biocompatible. Such embodiments are well suitable for implantation into tissue such as ophthalmic tissue for in vivo use.

In some embodiments, the hermetic electric interconnect 200 can be flexible. As discussed, this flexibility can reduce the size of the ophthalmic incisions necessary for inserting the optoelectronic device 100 into the eye. Furthermore, embodiments can adapt to body motion, tissue softness, and the potential evolution of the shape of the surrounding tissues.

In some embodiments, the hermetic electric interconnect 200 can be manufacturable by semiconductor batch fabrication technologies. Since semiconductor technologies are mature and efficient, adapting such techniques can produce reliable devices at low cost, with great control, and in extremely small sizes.

Figure 2:
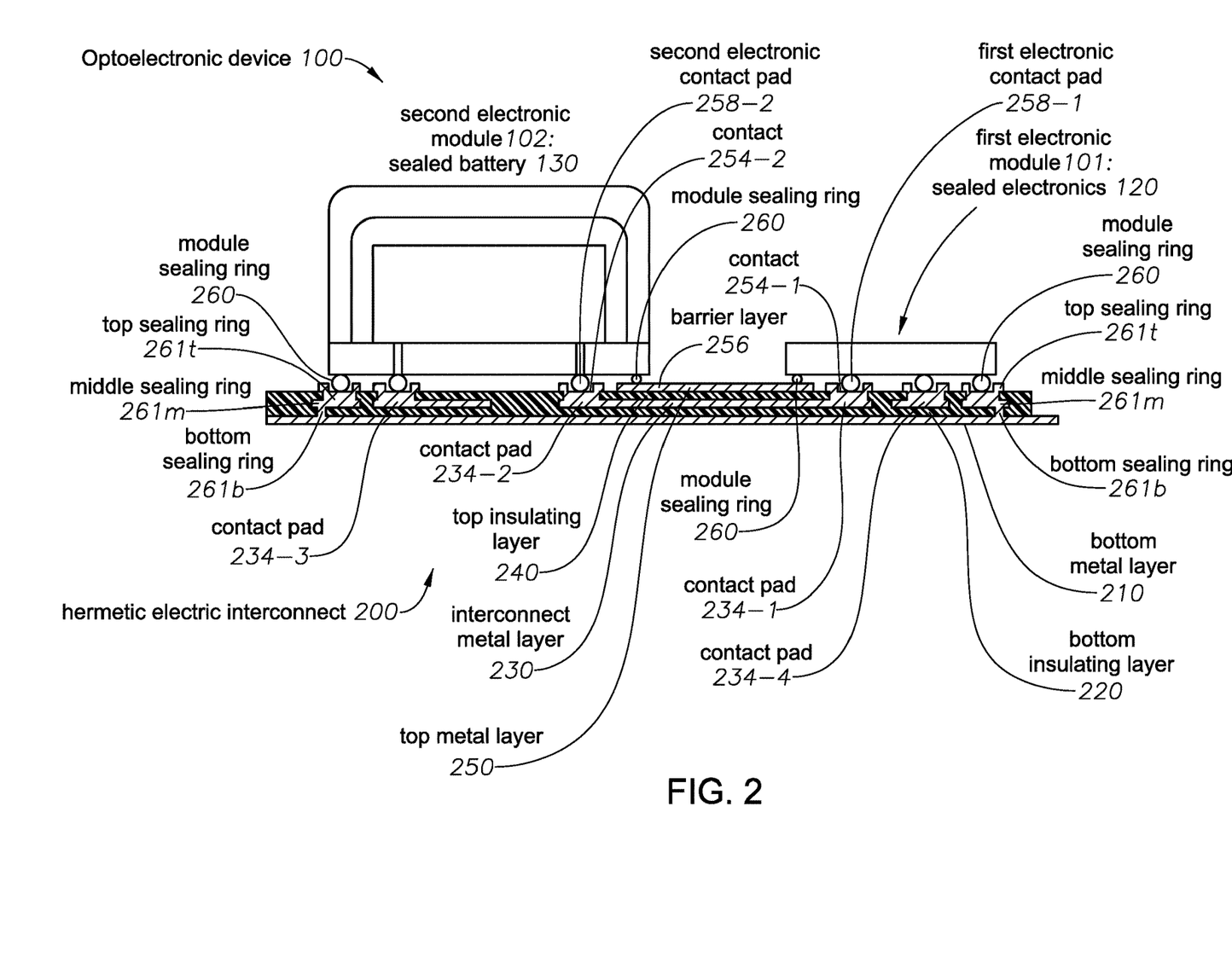
FIG. 2 illustrates a cross section of an optoelectronic device 100 with a hermetic electric interconnect 200.

FIG. 2 shows a cross section of an embodiment of the optoelectronic device 100 in some detail. As before, the device 100 can include a first electronic module 101 which in the present case is a sealed electronics 120, such as an integrated circuit, and a second electronic module 102 that in this case is a sealed battery pack 130. In other embodiments, one of the electronic modules can be the electroactive IOL 110. The hermetic electric interconnect 200 provides an electric connection between these two or more modules, and can include the following elements.

The hermetic electric interconnect 200 can include a bottom metal layer 210. This bottom metal layer 210 can be formed on a wafer, or substrate, which can be later removed.

The hermetic electric interconnect 200 can include a bottom insulating layer 220, deposited on the bottom metal layer 210 to insulate the bottom metal layer 210, and patterned to form a bottom seal ring trench 261*bt* (shown later in FIG. 4A for clarity).

The hermetic electric interconnect 200 can include an interconnect metal layer 230, deposited on the bottom insulating layer 220, and deposited to fill the bottom seal ring trench 261*bt* to form a bottom sealing ring 261*b*; and patterned to form electrical connections between contact pads 234-1 and 234-2, encircled by a middle sealing ring 261*m*, coupled with the bottom sealing ring 261*b*.

The hermetic electric interconnect 200 can include a patterned top insulating layer 240, deposited on the interconnect metal layer 230 to insulate the interconnect metal layer 230; and patterned to form feedthrough holes 242-1 and 242-2 (shown later in FIGS. 4B1-4B2 for clarity) for the contact pads 234-1 and 234-2, and to form a top seal ring trench 261*tt* (shown later in FIGS. 4B1-4B2 for clarity) coupled with the middle sealing ring 261*m*.

The hermetic electric interconnect 200 can include a top metal layer 250, deposited on the top insulating layer 240, and deposited to fill the feedthrough holes 242-1 and 242-2 to start forming contacts 254-1 and 254-2, and to fill the top seal ring trench 261*tt* to start forming a top sealing ring 261*t*; and patterned to complete forming contacts 254-1 and 254-2 through the feedthrough holes 242-1 and 242-2, to form a separate barrier layer 256, and to complete forming the top sealing ring 261*t*.

In some embodiments, the first and second electronic modules 101/120 and 102/130 can have electronic contact pads 258-1 and 258-2, and these electronic contact pads 258-1 and 258-2 can be seated into the contacts 254-1 and 254-2. Doing so establishes the electrical connection between the first and second electronic modules 101/120 and 102/130 via the hermetic electric interconnect 200.

In some embodiments, the device 100 can further include a module sealing ring 260, affixed to the first and second electronic modules 101/102 along a perimeter of the electronic modules. This module sealing ring 260 can be seated into and affixed to the top sealing ring 261*t* of the hermetic interconnect 200. In some embodiments, more than one module sealing ring 260 can be present, e.g., each electronic module 101/120 and 102/130 can have its own module sealing ring 260, as shown. In all of these embodiments, the top sealing ring 261*t* can be shaped to match the layout of the module sealing ring, or rings 260.

In embodiments, the bottom metal layer 210, the bottom sealing ring 261*b*, the middle sealing ring 261*m*, the top sealing ring 261*t*, the module sealing ring 260, sealing housings of the first and second electronic modules 101 and 102, and the barrier layer 256 can form a complete hermetic seal for the optoelectronic device 100.

The affixation of the module sealing ring 260 to the top sealing ring 261*t* can be performed by a wide variety of methods, such as thermomechanical bonding, a reflow process using a low melting temperature alloy, a laser-induced reflow through a transparent material, and ultrasonic bonding. An example of a suitable low melting temperature alloy is Au/Sn.

FIG. 2 concentrates on illustrating the electrical connection between contact pads 234-1 and 234-2, formed by the interconnect metal layer 230 that visibly connects them. In general, there can be several additional contact pads in embodiments, such as the shown contacts 234-3 and 234-4. Their electrical connections can be laid out in the plane of the interconnect metal layer 230 and therefore moving in and out of the plane of the cross section shown in FIG. 2. The contact pads 234-3 and 234-4 can be electrically connected by a trace formed in the interconnect metal layer 230, the trace exiting out of the plane of the cross section at contact pad 234-3 and re-entering the plane at contact pad 234-4. This is why contact pads 234-3 and 234-4 do not appear connected in the cross section of FIG. 2: they are connected through a trace that is outside the cross sectional plane. A top view of the layout of such additional electrical connections in the plane of the interconnect metal 230 is illustrated in FIG. 7B. For the ease of description, the remainder of this specification concentrates on the electrical connection between contact pads 234-1 and 234-2, but it is understood that the description also applies to the other, in front of the cross sectional plane and behind the cross sectional plane, electrical connections as well.

Figure 3:
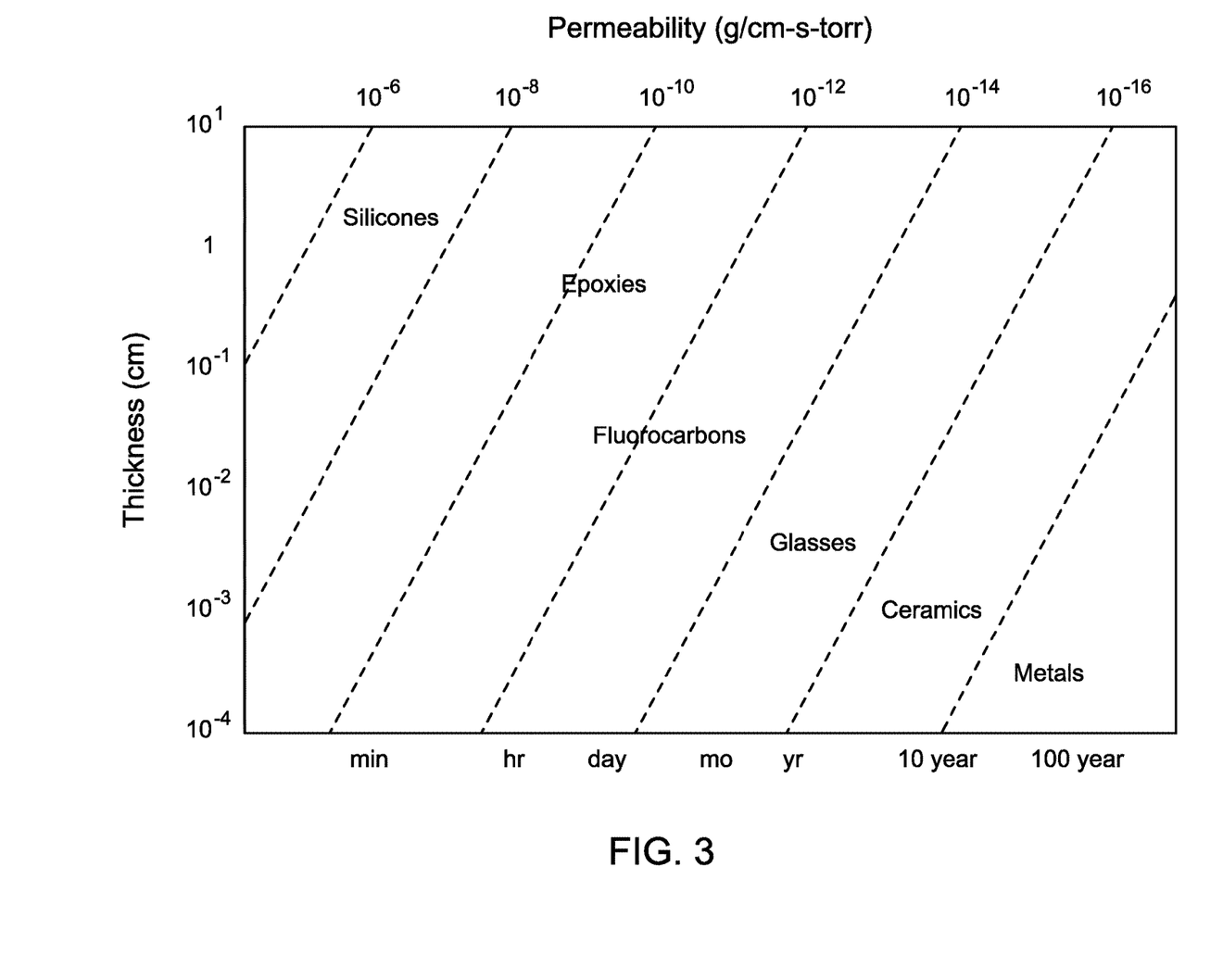
FIG. 3 illustrate chart of material properties.

FIG. 3 illustrates that in principle a wide variety of materials can be considered for the bottom metal layer 210. However, long term implantability into biological tissue sets stringent selection criteria. Embodiments of the eventual metal layer preferably should have (a) a low permeability, (b) over a very long period, (c) with a small layer thickness. Fulfilling these criteria is necessary to make sure that no moisture ingress or leakage occurs even 10 years after the implantation.

FIG. 3 shows that if the long term is set for 10 years or longer, then silicones, epoxies and polymers in general are unsuitable, and even glass requires several millimeter thickness to achieve the desired design performance. In an ophthalmic application, there is no room for a connection that is millimeters thick. Therefore, in embodiments of the interconnect 200, the bottom metal layer 210 is chosen as a metal or a ceramic. In embodiments, where a metal is used, the metal can have a permeability less than $10^{-14}$ g/(cm*sec*torr) at a metal thickness in a range of 0.5-1 micron, over a time period of at least 10 years. In other embodiments, the permeability can be less than $10^{-13}$ g/(cm*sec*torr), in yet other embodiments, $10^{-15}$ g/(cm*sec*torr), both at the same metal thickness in a range of 0.5-1 micron, over a time period of at least 10 years. Metals that satisfy these criteria, and are also biocompatible, include Ti, Au, Pt, or Nb. Therefore, embodiments of the bottom metal layer 210 can be formed using Ti, Au, Pt, or Nb or an alloy containing one or more of these metals.

While many embodiments of the optoelectronic device 100 will be mostly described in terms of the metal layers 210 and 250 being formed from metals, in other embodiments these same layers 210 and 250 can be formed from ceramics.

Also, embodiments of the bottom metal layer 210 can resist corrosion by a balanced saline solution (BSS) for at least ten years.

Further, the first and second insulating layers can be formed from a wide variety of insulating materials. Materials that can be photo-imaged are particularly suitable as using them can reduce the number of lithographic steps required for the fabrication of the optoelectronic device 100. Examples of such photo-imagable materials include polyimide. In other embodiments, non-photo-imagable materials can be used as well.

Figure 6A:
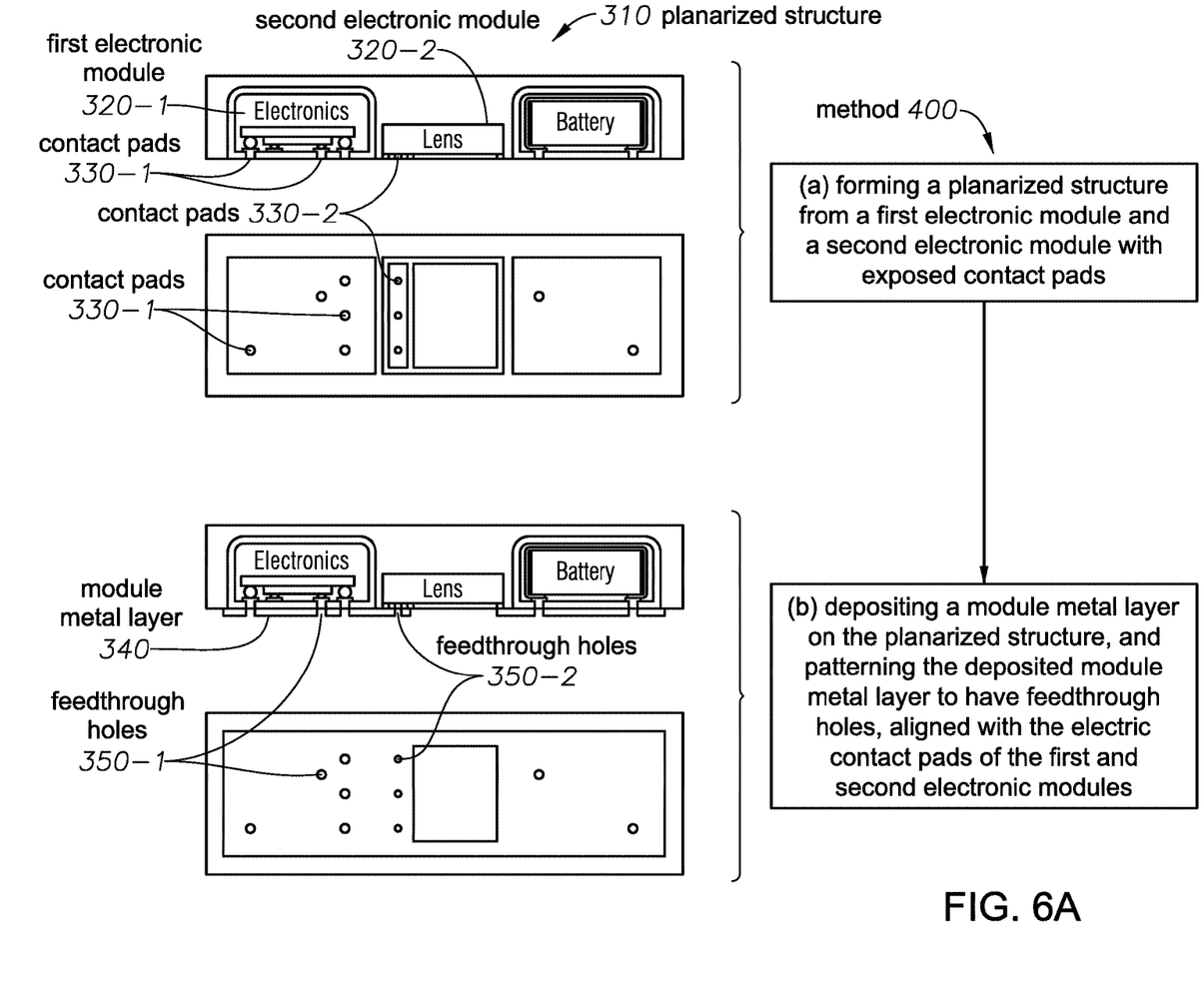
FIGS. 6A-C illustrate a method 400 of forming a hermetically sealed electric interconnect 200.
Figure 6B:
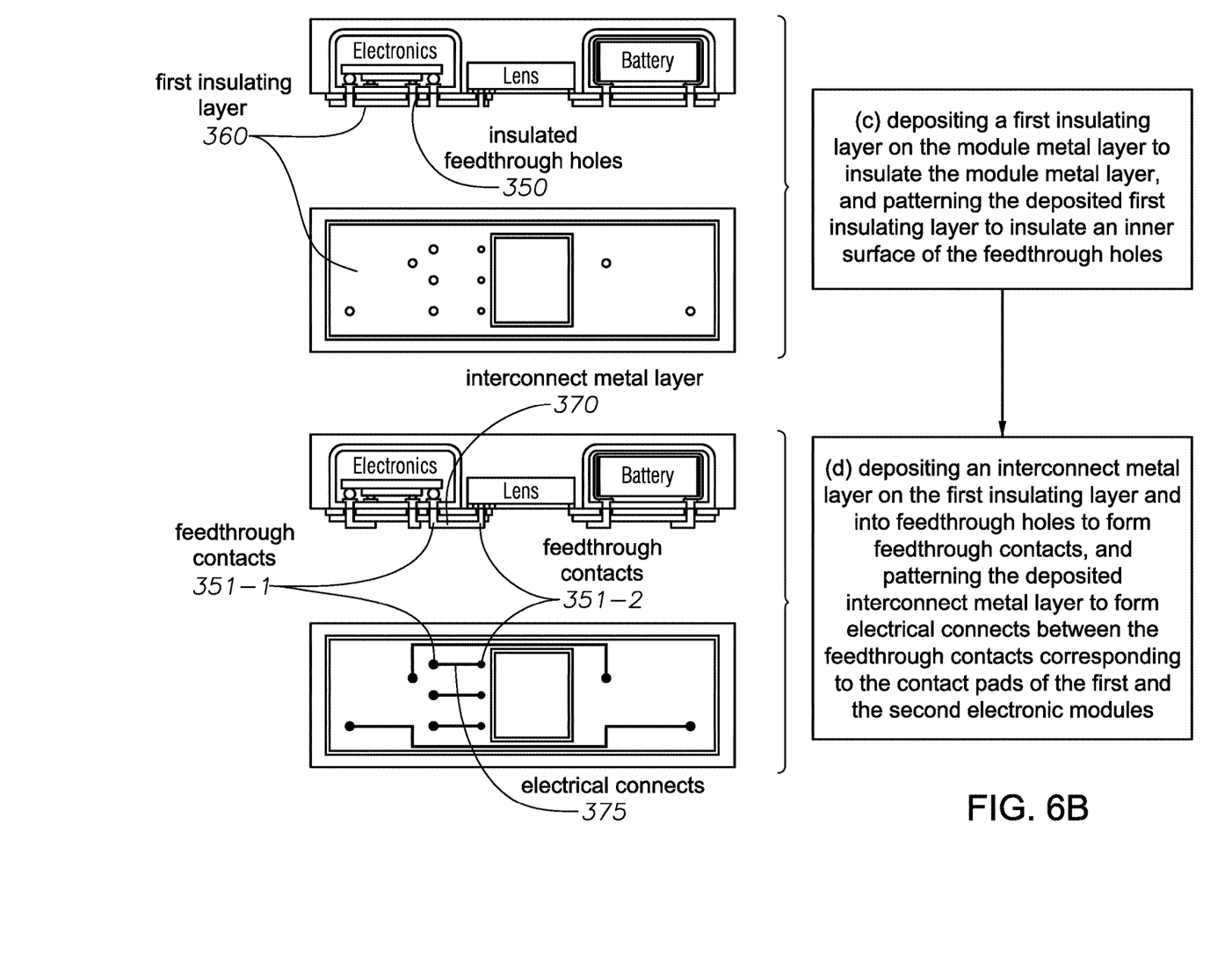
Figure 6C:
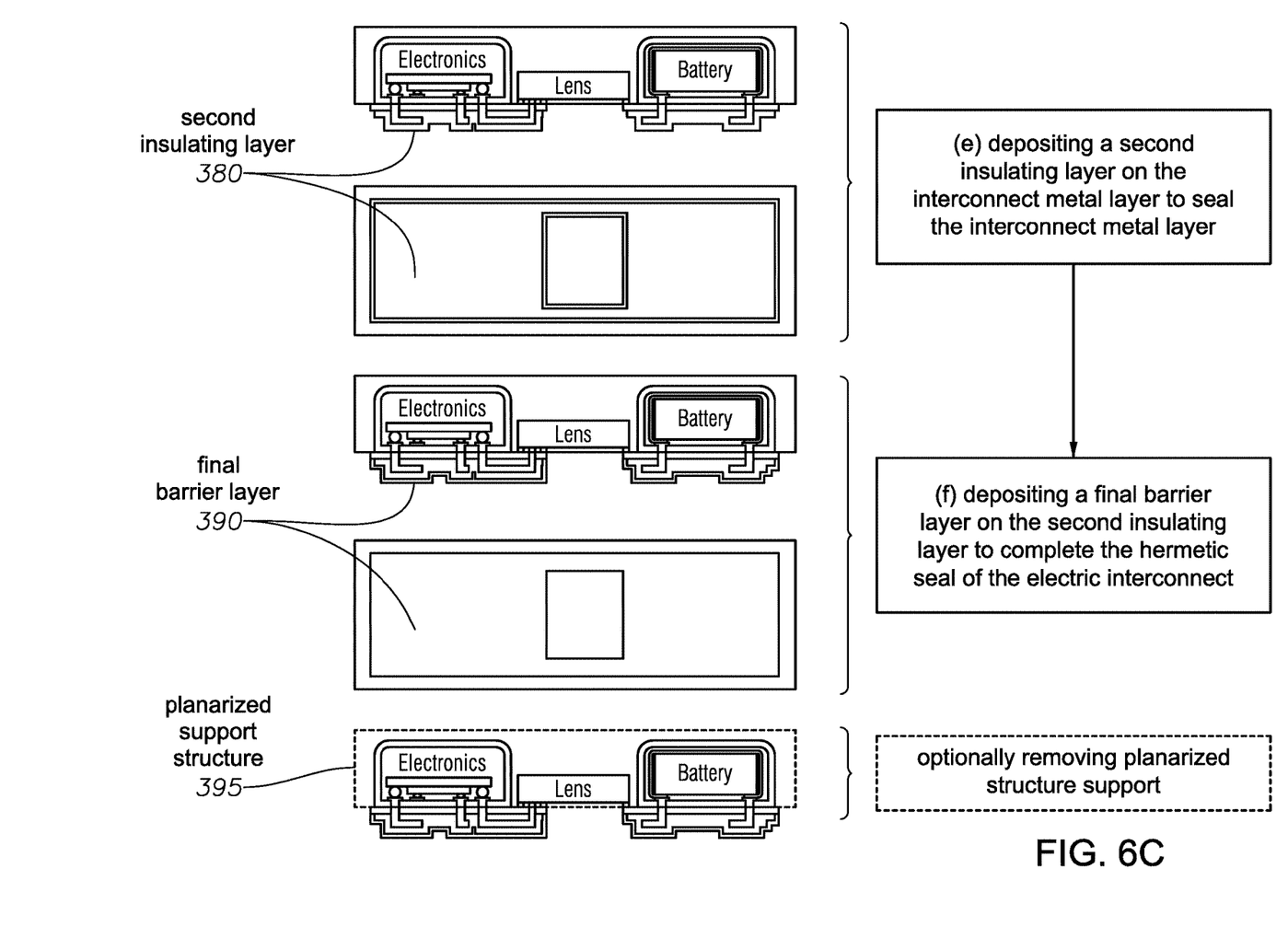

In some embodiments, the top insulating layer 240 has a stepped, "pyramidal" coverage pattern at a feedthrough hole to enhance a sealing efficiency. Such embodiments may have better sealing properties but their fabrication may require additional steps. An example of such embodiments will be described in some detail in relation to FIG. 6.

Figure 4A:
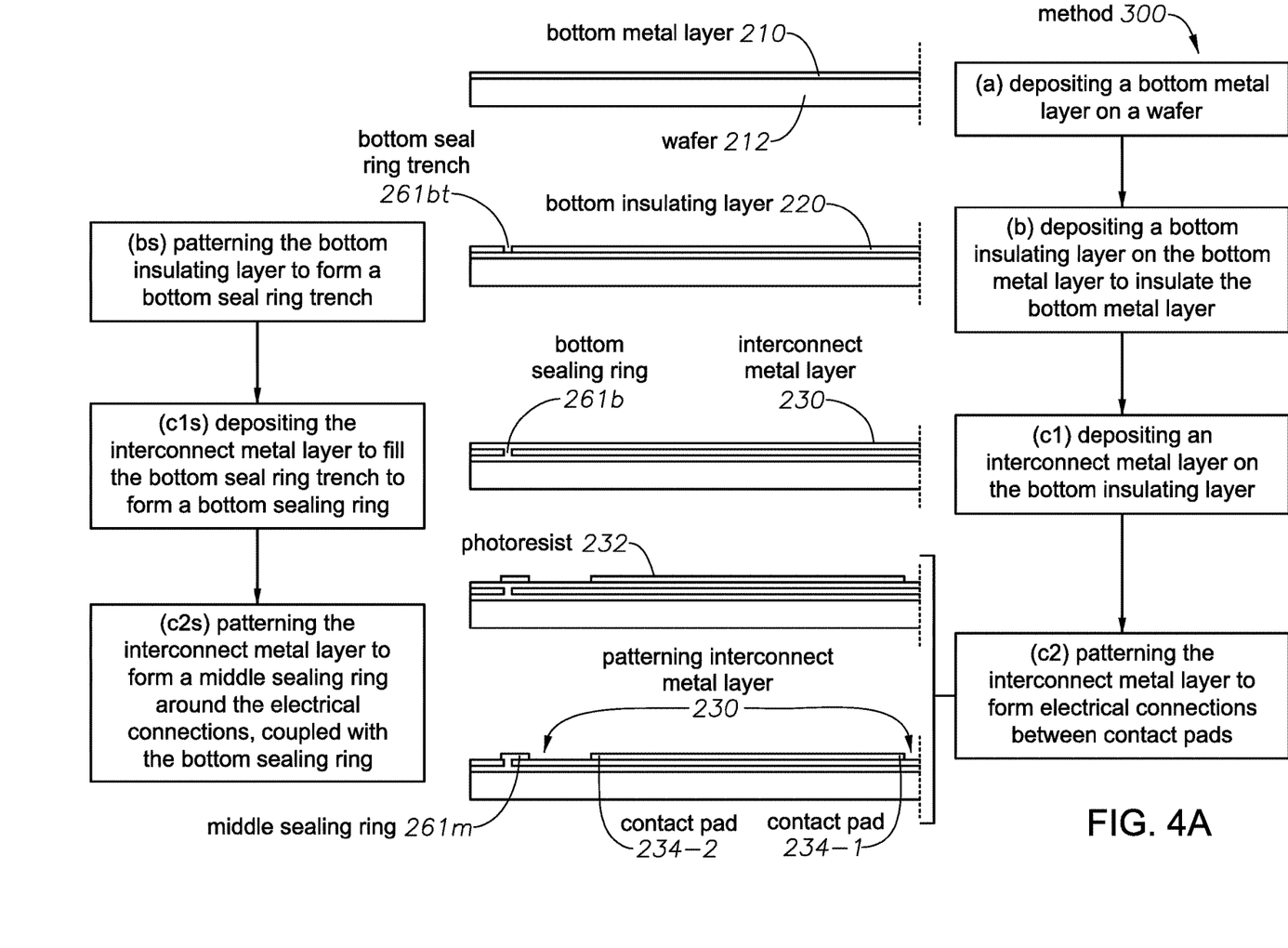
FIGS. 4A-B1-B2 illustrate a method 300 of forming a hermetically sealed electric interconnect 200.
Figure 4B:
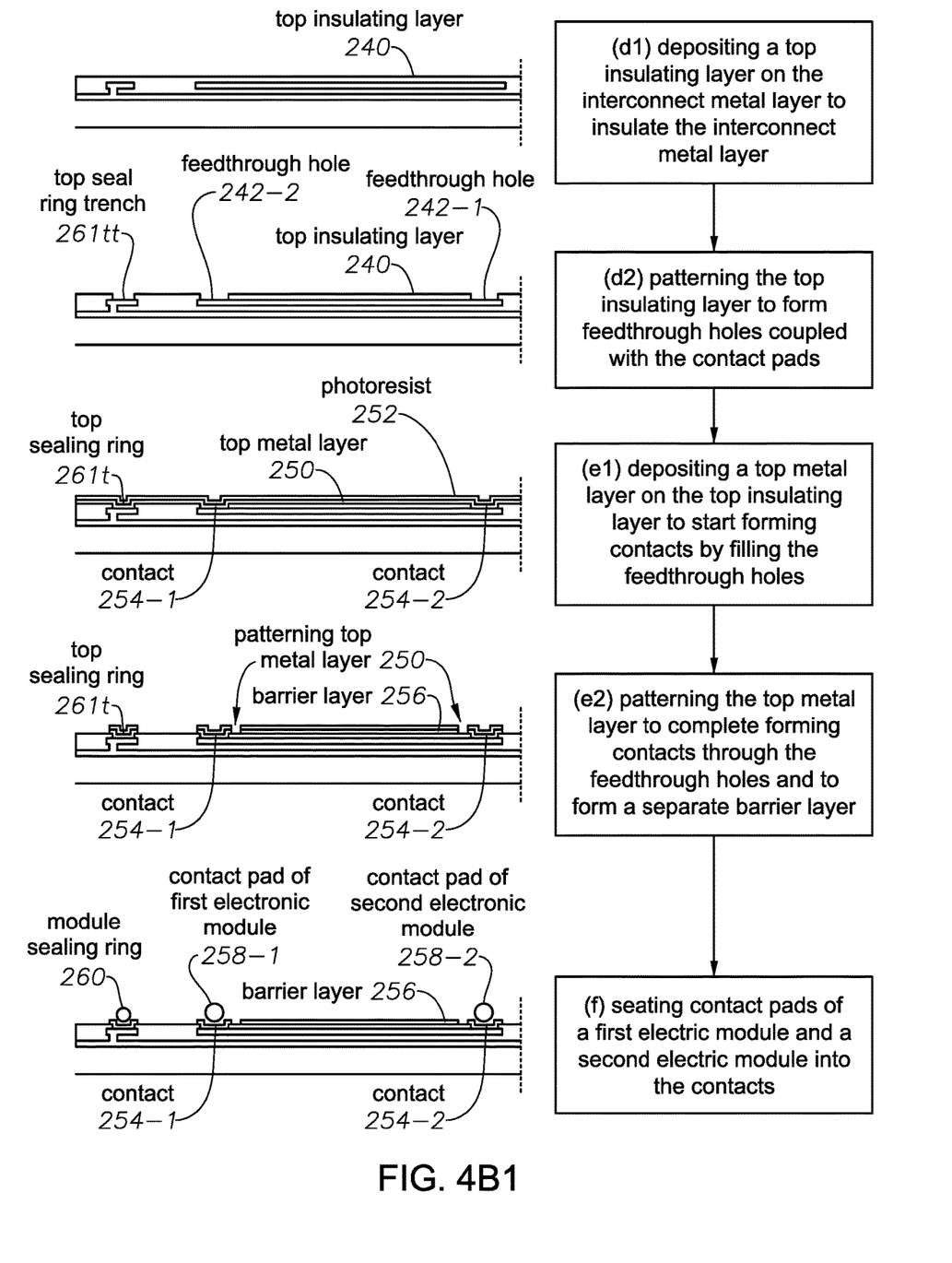
Figure 4B:
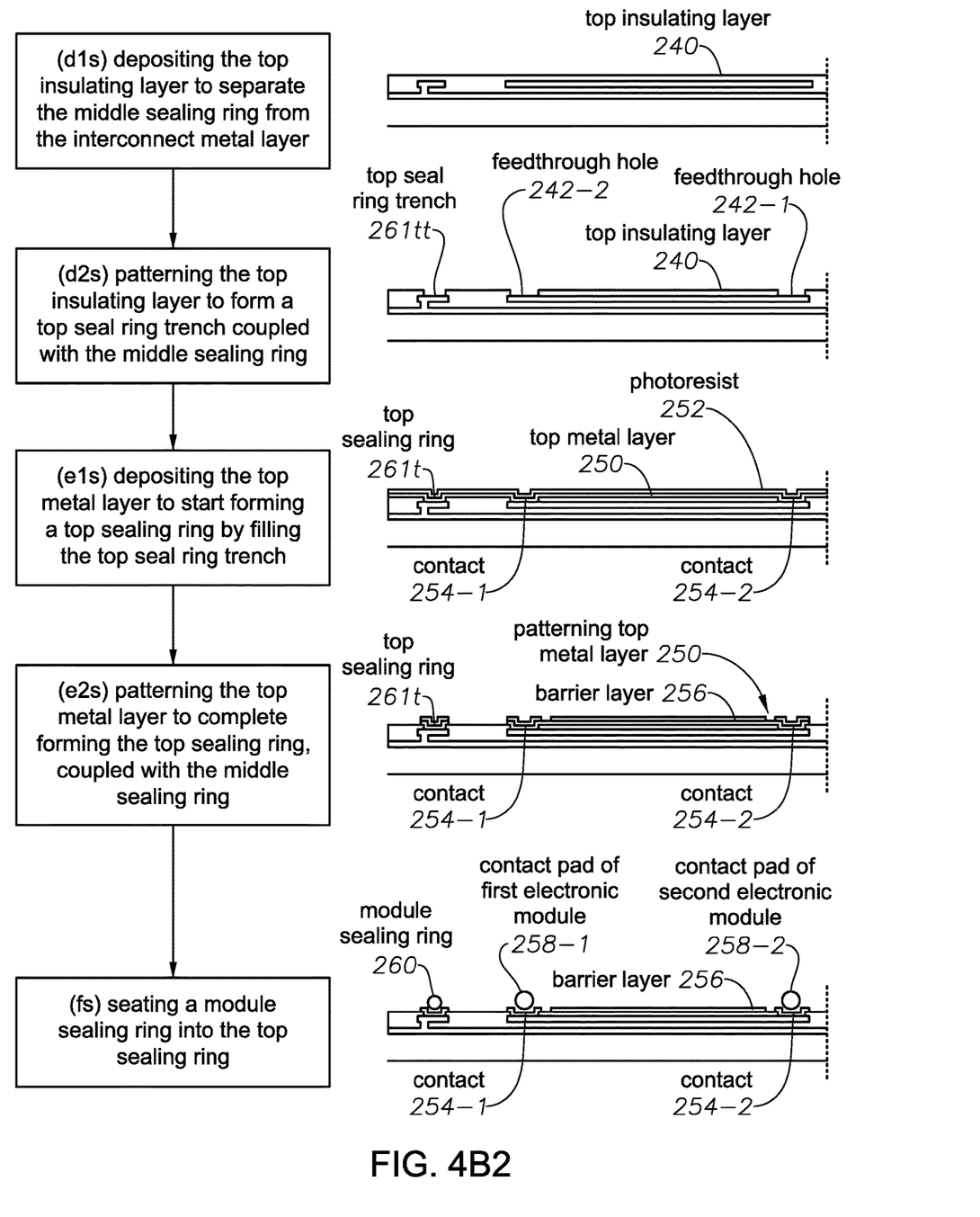

FIGS. 4A-B1-4B2 illustrate a method 300 of fabricating the hermetic electric connect 200. For clarity, FIGS. 4A-B1-B2 illustrate the steps in two columns. On the right hand side the steps (a, b, c), and the sub-steps (c1, d2) of the steps are shown that relate to the formation of the layers and electrical connections. On the left hand side, steps (bs, cs), and the sub-steps (c1*s*, d2*s*) of the steps are shown that relate to the formation of the seals. The formation of the electrical connections and the seals are performed in parallel, by patterning the layers for both purposes as they are deposited.

The optoelectronic device obviously has a seal structure on both edges. The seals on the right hand side are not shown in order to keep the figure less cluttered. Their presence is only referenced by the dotted line.

The method 300 can include the following steps.

Step 300(*a*)—Depositing a bottom metal layer 210 on a wafer (or substrate) 212. The substrate/wafer 212 can be silicon, for example <100>, n-type. As discussed, the metal used for this deposition step should satisfy the stringent criteria of a low permeability over 10 years or longer with a thickness in the range of 0.5-5 microns, such as about 1 micron. Examples of metals that satisfy these criteria include Ti, Au, Pt, and Nb. The thickness of the bottom metal layer 210 can be 0.5-2 microns. In some cases, this bottom metal layer 210 can in fact be made up of two metal layers, such as a 1 micron Au layer and a 500 Angstrom Ti layer.

Step 300(*b*)—Depositing a bottom insulating layer 220 on the bottom metal layer 210 to seal the bottom metal layer 210. The bottom insulating layer 220 can be deposited with spin coating, for example, with a thickness in the range of 0.5-5 microns, such as 1 micron. The bottom insulating layer can be a photo-imagable layer. In some embodiments, where the insulating layer 220 is such a photoresist, it can be patterned with a typical "exposing using a mask—developing the photoresist—heat treatment ('bake')" procedure. In other embodiments, the insulating layer 220 can be a non-photoresist layer, in which case the patterning is done by lithographic procedures that involve depositing an additional separate photoresist layer, followed by the exposing, developing and etching steps.

Step 300(*bs*)—Patterning the bottom insulating layer 220 to form a bottom seal ring trench 261*bt*. This bottom seal ring trench 261*bt* can be a small notch with a ring layout, encircling the footprint of the planned electrical connections.

Step 300(*c*1)—Depositing an interconnect metal layer 230 on the bottom insulating layer 220 to insulate the bottom insulating layer 220. The interconnect metal layer 230 can be deposited with sputtering, for example. Its thickness can be 0.5-5 microns, such as 1 micron. The metal layer 230 can be made of Au, Ti, or equivalents.

Step 300(*c*1*s*)—Depositing the interconnect metal layer 230 to fill the bottom seal ring trench 261*bt* to form a bottom sealing ring 261*b*.

Step 300(*c*2)—Patterning the interconnect metal layer 230 to form electrical connections between contact pads 234-1 and 234-2. The patterning can be performed by depositing a photoresist 232, exposing it using an interconnect mask, then developing the photoresist 232, removing the unexposed portions and then etching away the interconnect metal layer 230 to form the desired pattern. In FIG. 4A a simple linear electrical connection is formed between contact pads 234-1 and 234-2. FIG. 7B illustrates the formation of a two dimensional more complex electrical connection pattern.

Step 300(*c*2*s*)—Patterning the interconnect metal layer 230 to form a middle sealing ring 261*m* around the electrical connections, coupled with the bottom sealing ring 261*b*.

FIGS. 4B1-4B2 illustrate step 300(*d*1)—Depositing a top insulating layer 240 on the interconnect metal layer 230 to insulate the interconnect metal layer 230.

Step 300(*d*1*s*)—Depositing the top insulating layer 240 to separate the middle sealing ring 261*m* from the interconnect metal layer 230.

Step 300(*d*2)—Patterning the top insulating layer 240 to form feedthrough holes 242-1 and 242-2, coupled with the contact pads 234-1 and 243-2. The patterning of the top insulating layer 240 can be performed with the usual methods of depositing a photoresist—exposing the photoresist with a feedthrough mask—developing the photoresist—etching the feedthrough holes 242 into the top insulating layer 240. In some embodiments, the top insulating layer can be a photoresist itself, requiring fewer procedure steps.

Step 300(*d*2*s*)—Patterning the top insulating layer 240 to form a top seal ring trench 261*tt* coupled with the middle sealing ring 261*m*.

Step 300(*e*1)—Depositing a top metal layer 250 on the top insulating layer 240 to start forming contacts 254-1 and 254-2 by filling the feedthrough holes 242-1 and 242-2.

Step 300(*a*1*s*)-(*e*1*s*) depositing the top metal layer 250 to start forming a top sealing ring 261*t* by filling the top seal ring trench 261*tt*.

Step 300(*e*2)—Patterning the top metal layer 250 to complete forming contacts 254-1 and 254-2 through the feedthrough holes 242-1 and 242-2, as well as to form a separate barrier layer 256 to serve as a moisture barrier and insulation for the overall interconnect 200. The barrier layer 256 can also provide structural strength. As usual, the patterning of the top metal layer 250 can be performed by depositing and exposing a photoresist 252, followed by an etching step. The etching can separate the top metal layer 250 into the barrier layer 256 that is not coupled electrically to the interconnect metal layer 230, and into the contacts 254-1 and 254-2 that are electrically coupled to the interconnect metal layer 230 through the feedthrough holes 242-1 and 242-2. As shown in FIG. 2, these contacts 254-1 and 254-2 can have the shape of a cradle.

Step 300(*e*2*s*)—Patterning the top metal layer 250 to complete forming the top sealing ring 261*t*, coupled with the middle sealing ring. The top sealing ring 261*t* can have a shape quite similar to the contacts 254, with the key difference being that it is electrically isolated from the interconnect metal layer 230 as its function is sealing and protection. As shown, in some cases the top sealing ring 261*t* can have a cradle shape. The top sealing ring 261*t* can be coupled to the middle sealing ring 261*m* and run around the entire perimeter of the interconnect 200 in a closed loop to complete the protection. In some embodiments, there are separate top sealing rings 261*t* around the first and the second electronic modules 101 and 102.

Step 300(*f*)—Seating contact pads 258-1 and 258-2 of a first electronic module 101 and a second electronic module 102 on the contacts 254-1 and 254-2.

Step 300(*fs*)—Seating a module sealing ring 260 into the top sealing ring 261*t*. This step 300(*fs*) completes the sealing around the perimeter of the hermetic electric interconnect 200 in some embodiments.

While the description in this document articulated the embodiments in terms of two contacts 254-1 and 254-2, obviously in a variety of embodiments the number of contacts can be substantially more. For example, the embodiment of FIG. 7B illustrates a design where 10 different contacts are electrically connected by the hermetic electric interconnect 200.

Figure 5:
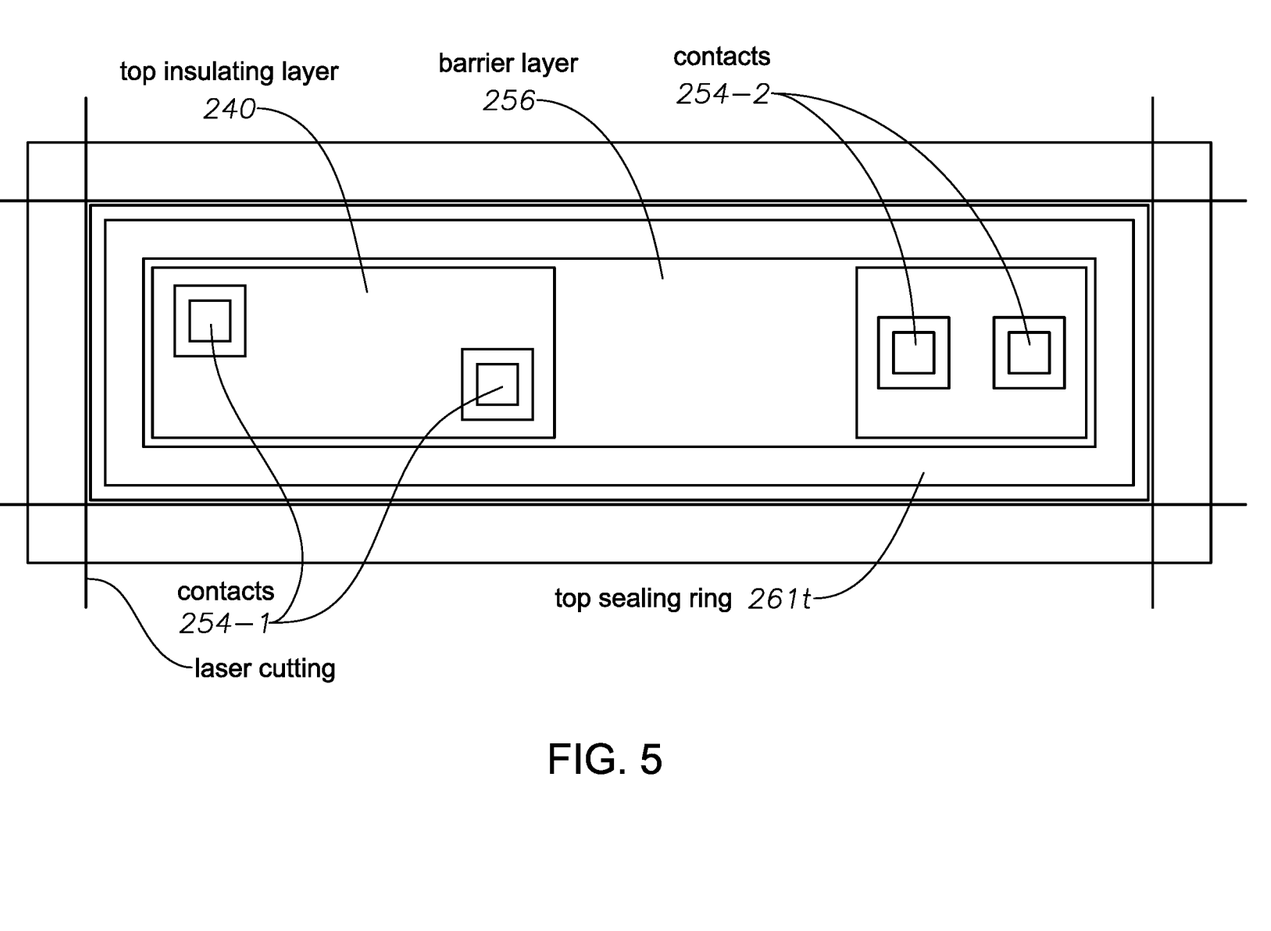
FIG. 5 illustrates a top view of a hermetically sealed electric interconnect 200, created by the method 300.

FIG. 5 illustrates a top view of the interconnect 200 fabricated by the method 300. The contacts 254-1 and 254-2 are shown: in this embodiment there are two of each of these contacts. Beneath the plane of FIG. 5, these four contacts 254-1 and 254-2 are pairwise electrically connected by the patterned interconnect metal layer 230.

These contacts 254 are surrounded by the top insulating layer 240. Where the top surface is, or can be exposed to biological tissue, the top is covered by the barrier layer 256. Finally, the top sealing ring 261*t* is shown to form a ring around the entire outer perimeter of the arrangement.

In some embodiments, the depositing of the interconnect metal layer 230, the bottom metal layer 210 and the top metal layer 250 can include sputtering. The deposited bottom metal layer 210 and top metal layer 250 can include Ti, Au, Pt, or Nb, or their alloys.

Also, in some embodiments, the depositing and patterning the bottom insulating layer 220 and the top insulating layer 240 can include spin-coating, spray coating, or lamination.

As shown, at the outer edges un-needed portions of the formed layers can be cut away, for example, by laser cutting.

FIGS. 6A-C illustrate a method 400 for fabricating an embodiment of the hermetic electric interconnect 200 for an optoelectronic device 100. The method 300 starts a deposition sequence with the layer that is farthest from the contact plane with the electronic modules, the bottom metal layer 210. As an alternative, the now-described method 400 starts with depositing a layer that is closest to the contact plane with the electronic modules. In this sense, methods 300 and 400 are complimentary to each other. They can be also referred to as bottom-up and top-down procedures, respectively. Method 400 can include the following steps. For each step, a side view and a bottom view is provided for enhanced clarity.

Step 400(a)—Forming a planarized structure 310 from at least a first electronic module 101/320-1 and a second electronic module 102/320-2 with exposed electronic contact pads 330-1 and 330-2. As before, the first and second electronic modules 101/320-1 and 102/320-2 can be any one of the electroactive IOL 110, the electronics 120, or the battery stack 130. In the shown embodiment, the planarized structure 310 is formed from all three electronic modules 110, 120, and 130. As before, while only one contact pad is explicitly described per electronic module, various embodiments can have several more contact pads.

Possible ways to forming the planarized structure 310 will be described in relation to FIG. 7.

Step 400(b)—Depositing a module metal layer 340 on the planarized structure 310, and patterning the deposited module metal layer 340 to have feedthrough holes 350-1 and 350-2, coupled with the electronic contact pads 330-1 and 330-2 of the first and second electronic modules 101/320-1 and 102/320-2. In embodiments, the number of feedthrough holes 350 can be the same as the number of contact pads 330.

FIG. 6B illustrates step 400(c)—Depositing a first insulating layer 360 on the module metal layer 340 to insulate the module metal layer 340, and patterning the deposited first insulating layer 360 to insulate an inner surface of the feedthrough holes 350-1 and 350-2.

Step 400(d)—Depositing an interconnect metal layer 370 on the first insulating layer 360 and into feedthrough holes 350-1 and 350-2 to form contacts 351-1 and 351-2, and patterning the deposited interconnect metal layer 370 to form electrical connects 375 between the contacts 351-1 and 351-2 corresponding to the contact pads of the first and the second electronic modules 101/320-1 and 102/320-2.

FIG. 6C illustrates step 400(e)—Depositing a second insulating layer 380 on the interconnect metal layer 370 to seal the interconnect metal layer 370.

Step 400(f)—Depositing a final barrier layer 390 on the second insulating layer 380 to complete the hermetic seal of the electric interconnect 200.

The method 400 can include the optional step of removing a planarized structure support 395 that was used to form the planarized structure 310 in step 400(a).

Figure 7:
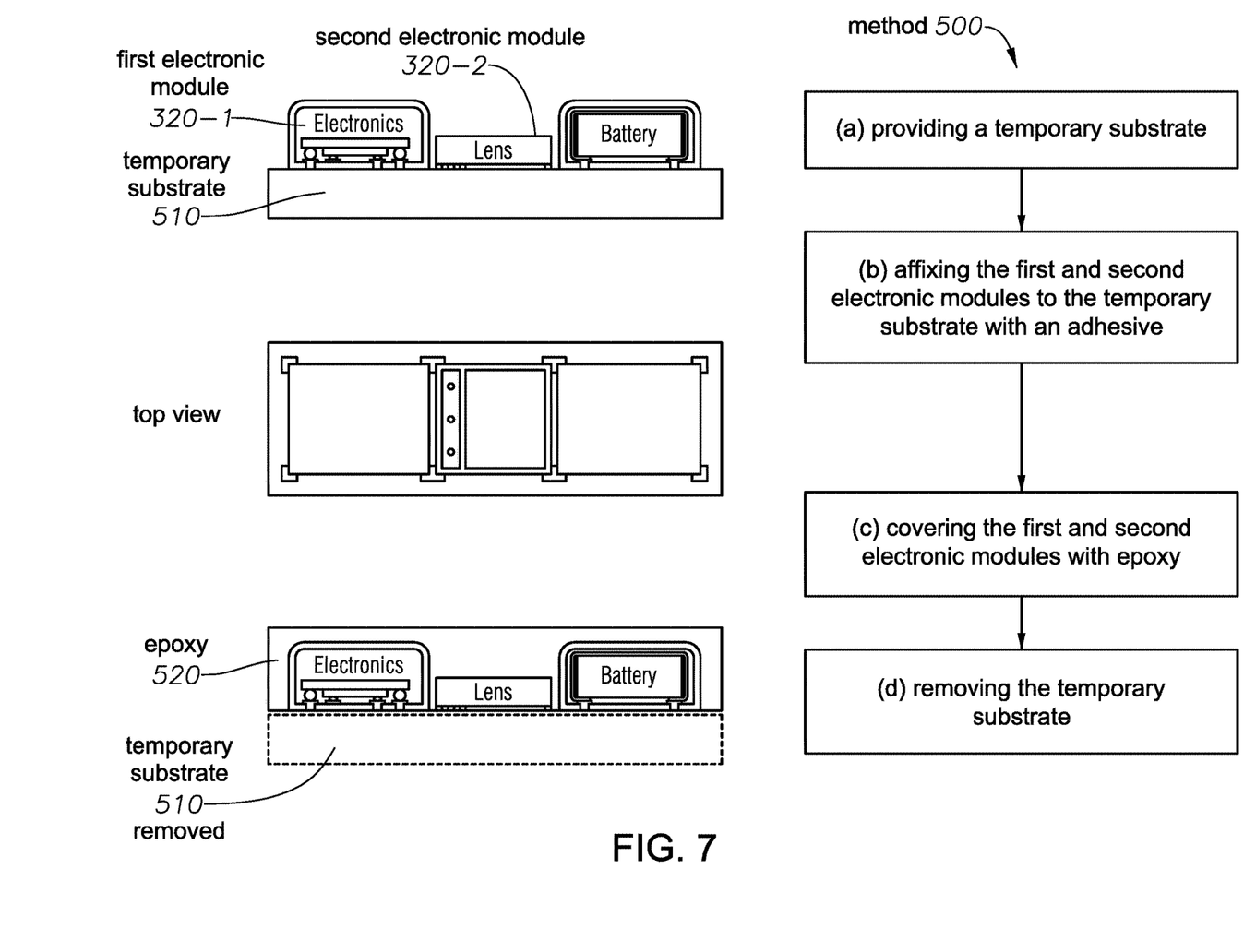
FIG. 7 illustrates a method 500 for forming a planarized structure 310.

FIG. 7 illustrates a method 500, an embodiment of the preparatory step 400(a) in some detail. The method 500 of forming the planarized structure can include the following steps.

Step 500(a)—Providing a temporary substrate 510.

Step 500(b)—Affixing the first and second electronic modules 101/320-1 and 102/320-2 to the temporary substrate 510 with an adhesive.

Step 500(c)—Covering the first and second electronic modules 101/320-1 and 102/320-2 with an epoxy 520. This epoxy can be an embodiment of the planarized structure support 395 of method 400.

Step 500(d)—Removing the temporary substrate 510.

As for the method 400, in some embodiments, the depositing the interconnect metal layer 370 in step 400(d) can be performed with sputtering; and the depositing the first insulating layer 360 in step 400(c) or the depositing the second insulating layer 380 in step 400(e) can be performed with spin-coating.

The step 400(b) of the depositing the module metal layer 340 and step 400(f) of the depositing the final barrier layer 390 can include depositing a metal layer including at least one of Ti, Au, Pt, and Nb.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a sub combination.

The invention claimed is:

1. An electronic device, comprising:
   a first electronic module;
   a second electronic module; and
   a hermetic electric interconnect to provide a hermetically sealed electric coupling between the first and second electronic modules, wherein the hermetic electric interconnect comprises:
      a bottom metal layer,
      a bottom insulating layer, deposited on the bottom metal layer to insulate the bottom metal layer, and patterned to form a bottom seal ring trench,
      an interconnect metal layer, deposited on the bottom insulating layer, and deposited to fill the bottom seal ring trench to form a bottom sealing ring; and patterned to form electrical connections between contact pads, and to form a middle sealing ring around the electrical connections, coupled with the bottom sealing ring,
      a patterned top insulating layer, deposited on the interconnect metal layer to insulate the interconnect metal layer, and to separate the middle sealing ring from the interconnect metal layer; and patterned to form feedthrough holes for the contact pads, and to form a top seal ring trench coupled with the middle sealing ring, and
      a top metal layer, deposited on the top insulating layer to start forming contacts by filling the feedthrough holes, and deposited to start forming a top sealing ring by filling the top seal ring trench; and patterned to complete forming contacts through the feedthrough holes, to form a separate barrier layer, and to complete forming the top sealing ring.

2. The device of claim 1, wherein:
   the first electronic module and the second electronic module are selected from the group comprising of a battery pack, an electroactive Intra-Ocular Lens, an electronics module, and a hermetically sealed enclosure of a combination of integrated circuits and devices.

3. The device of claim 1, wherein:
the hermetic electric interconnect is biocompatible.

4. The device of claim 1, wherein:
the hermetic electric interconnect is flexible.

5. The device of claim 1, wherein:
the hermetic electric interconnect is manufacturable by semiconductor batch fabrication technologies.

6. The device of claim 1, wherein:
the first and second electronic modules have electronic contact pads; and
the electronic contact pads of the first and second electronic modules are seated into the contacts.

7. The device of claim 1, further comprising:
a module sealing ring, affixed to the first and second electronic modules along a perimeter of the electronic modules, and seated into the top sealing ring of the hermetic electric interconnect.

8. The device of claim 7, wherein:
the module sealing ring is formed by one of thermomechanical bonding, a reflow process using a low melting temperature alloy, a laser-induced reflow through a transparent material, and ultrasonic bonding.

9. The device of claim 8, wherein:
the bottom metal layer, the bottom sealing ring, the middle sealing ring, the top sealing ring, the module sealing ring, sealing housings of the first and second electronic modules, and the barrier layer form a complete hermetic seal.

10. The device of claim 1, at least one of the bottom metal layer and the top metal layer comprising:
at least one of Ti, Au, Pt, Nb, and an alloy of one or more of these metals.

11. The device of claim 1, at least one of the bottom metal layer and the top metal layer comprising:
a metal capable of resisting corrosion by a balanced saline solution for at least ten years.

12. The device of claim 1, at least one of the bottom metal layer and the top metal layer comprising:
a metal with a permeability less than $10^{-14}$ g/(cm*sec*torr) at a thickness in a range of 0.5 to 1 micron, over at least 10 years.

13. The device of claim 1, the bottom insulating layer and the top insulating layer comprising:
photo-imagable polyimide.

14. The device of claim 1, wherein:
the top insulating layer has a stepped coverage pattern at a feedthrough hole to enhance a sealing efficiency.

* * * * *